United States Patent [19]
O'Brien et al.

[11] Patent Number: 5,461,049
[45] Date of Patent: Oct. 24, 1995

[54] AMIDE TETRAZOLE ACAT INHIBITORS

[75] Inventors: Patrick M. O'Brien, Stockbridge; Drago R. Sliskovic, Ypsilanti, both of Mich.

[73] Assignee: Warner-Lambert Company, Morris Plains, N.J.

[21] Appl. No.: 250,411

[22] Filed: May 27, 1994

[51] Int. Cl.$^6$ .................. A61K 31/41; C07D 257/04
[52] U.S. Cl. .................. 514/212; 514/227.8; 514/236.2; 514/241; 514/248; 514/252; 514/256; 514/259; 514/300; 514/310; 514/313; 514/314; 514/326; 514/381; 514/382; 540/603; 544/60; 544/132; 544/180; 544/235; 544/237; 544/284; 544/322; 544/328; 544/366; 546/121; 546/122; 546/162; 546/163; 546/171; 546/143; 546/210; 546/276; 548/251; 548/253
[58] Field of Search .................. 548/251, 253; 514/381, 212, 227.8, 236.2, 248, 252, 256, 259, 300, 241, 310, 313, 314, 326, 382; 540/603; 544/60, 132, 180, 235, 237, 284, 322, 328, 366; 546/121, 122, 162, 163, 171, 143, 210, 276

[56] References Cited

U.S. PATENT DOCUMENTS

| | | | |
|---|---|---|---|
| 4,540,703 | 9/1985 | Uchida et al. | 514/381 |
| 5,015,644 | 5/1991 | Roth et al. | 514/247 |
| 5,073,565 | 12/1991 | Chucholowski et al. | 514/381 |
| 5,116,848 | 5/1992 | Trivedi | 514/332 |

FOREIGN PATENT DOCUMENTS

| | | |
|---|---|---|
| 0035046 | 9/1981 | European Pat. Off. . |
| 0570245 | 11/1993 | European Pat. Off. . |
| 9117150 | 11/1991 | WIPO . |
| 9201675 | 2/1992 | WIPO . |
| 9304052 | 3/1993 | WIPO . |

OTHER PUBLICATIONS

Spector, et al., *Prog. Lipid Res.*, vol. 18, pp. 31–53, 1979.

*Primary Examiner*—Philip I. Datlow
*Attorney, Agent, or Firm*—Charles W. Ashbrook; Todd M. Crissey

[57] ABSTRACT

Amide tetrazoles of the formula

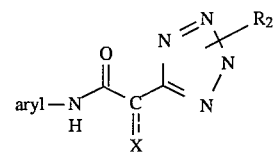

wherein aryl includes phenyl and naphthyl, unsubstituted or substituted, X is =O, =N—$R_5$, or —$NR_3R_4$, where $R_2$, $R_4$, and $R_5$ include alkyl and alkoxy and $R_3$ includes alkyl, are potent inhibitors of the enzyme acyl CoA:cholesterol acyltransferase (ACAT) and are thus useful for treating hypercholesterolemia or atherosclerosis.

23 Claims, No Drawings

AMIDE TETRAZOLE ACAT INHIBITORS

BACKGROUND OF THE INVENTION

This invention provides new chemical compounds characterized as being amide tetrazoles. The compounds inhibit acyl-CoA: cholesterol acyltransferase (ACAT), the enzyme responsible for the esterification of dietary cholesterol. Such agents thus decrease the absorption of dietary cholesterol and therefore provide a therapy for individuals with hypercholesterolemia and atherosclerosis.

High levels of cholesterol have been associated with heightened risk for development of several disease states, most notably coronary heart disease. A great deal of effort has been devoted to finding ways to lower cholesterol levels in biological systems. The approach of lowering cholesterol intake by modifying diet has met with only limited success. The ACAT enzyme is known to catalyze the esterification of dietary cholesterol, and has been implicated in several aspects of the atherosclerotic process in animals. One approach to lowering cholesterol then is to inhibit the ACAT enzyme. While several ACAT inhibitors have been identified (see for example EP 0570245), the need continues to identify and develop new ACAT inhibitors having improved therapeutic properties.

An object of this invention is therefore to provide a new series of compounds which are tetrazole derivatives and which have demonstrated excellent ACAT inhibitory properties. Another object is to provide pharmaceutical formulations comprising the tetrazoles and a carrier or excipient, and a method for inhibiting the ACAT enzyme by administering a compound of the invention.

SUMMARY OF THE INVENTION

This invention concerns new compounds which are amide tetrazoles and which inhibit the ACAT enzyme. The compounds of the invention have the Formula I

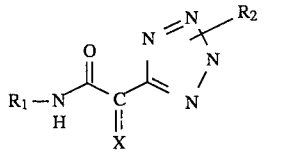

wherein $R_1$ is selected from
(a) phenyl which is unsubstituted or is substituted with from 1 to 3 substituents selected from
  $C_1-C_4$ alkyl,
  $C_1-C_4$ alkoxy,
  $C_1-C_4$ alkylthio,
  hydroxy,
  halo,
  nitro,
  cyano,
  trifluoromethyl,
  —COOH,
  —COOalkyl wherein alkyl has from 1 to 4 carbon atoms and which is straight or branched,
  —$(CH_2)_m NR_x R_y$ wherein m is 0 or 1, and each of $R_x$ and $R_y$ is independently hydrogen or $C_1-C_4$ alkyl;
(b) 1- or 2-naphthyl which is unsubstituted or substituted with from 1 to 3 substituents selected from
  $C_1-C_4$ alkyl,
  $C_1-C_4$ alkoxy,
  $C_1-C_4$ alkylthio,
  hydroxy,
  halo,
  nitro,
  cyano,
  trifluoromethyl,
  —COOH,
  —COOalkyl wherein alkyl has from 1 to 4 carbon atoms and which is straight or branched,
  —$(CH_2)_m NR_x R_y$ wherein m is 0 or 1, and each of $R_x$ and $R_y$ is independently hydrogen or $C_1-C_4$ alkyl;
(c) the group

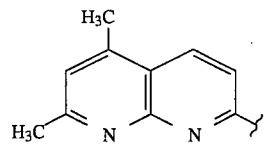

(d) the group

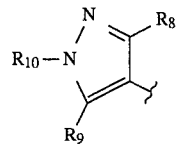

wherein $R_8$ and $R_9$ independently are $C_1-C_4$ alkyl or phenyl, and $R_{10}$ is a straight or branched hydrocarbon group having from 1 to 18 carbon atoms which is saturated or is unsaturated containing one double bond or two nonadjacent double bonds; phenyl; phenyl substituted with from 1 to 3 substituents selected from
  $C_1-C_4$ alkyl,
  $C_1-C_4$ alkoxy,
  hydroxy,
  halo,
  nitro,
  cyano,
  trifluoromethyl,
  —COOH,
  —COOalkyl wherein alkyl has from 1 to 4 carbon atoms and is straight or branched,
  —$(CH_2)_m NR_x R_y$ wherein m, $R_x$, and $R_y$ are as defined above; or
  a heterocyclic group selected from 2-, 3-, or 4-pyridyl, 2-, 4-, or 5-pyrimidinyl, 2-, or 3-pyrazinyl, 2-, 3-, 4-, 5-, 6-, 7-, or 8-quinolinyl, 3- or 4-pyridazinyl, and the N-oxides thereof;
(e) the group

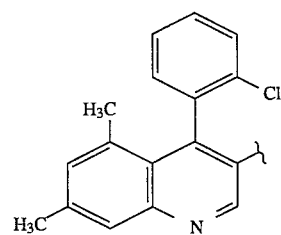

(f) a straight or branched hydrocarbon group having from 1 to 18 carbon atoms which is saturated or is unsaturated containing one double bond or two nonadjacent double bonds;

(g) a cycloalkyl group having from 3 to 10 carbon atoms;
(h) the group

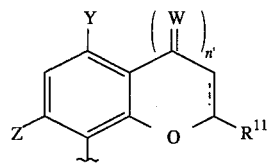

wherein — denotes a single or double bond;
Y and Z are each independently hydrogen, $C_1$–$C_4$ alkyl, $C_1$–$C_4$ alkoxy, or halo;
W is oxygen or two hydrogen atoms;
$R^{11}$ is hydrogen or $C_1$–$C_4$ alkyl, and n' is 0 or 1; or
(i) is selected from the group

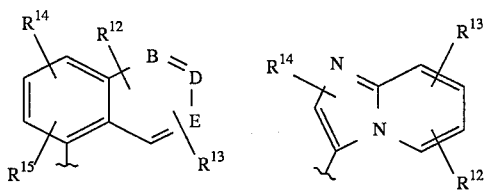

and

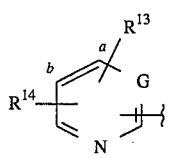

wherein $R^{12}$, $R^{13}$, $R^{14}$, and $R^{15}$ are each independently
hydrogen,
halo,
$C_1$–$C_4$ alkyl,
$C_1$–$C_4$ alkoxy,
$C_1$–$C_4$ alkylthio,
cycloalkylthio of 5 to 7 carbon atoms,
phenylalkylthio in which alkyl is 1 to 4 carbon atoms,
substituted phenylthio, heteroarylthio, or heteroaryloxy;
and B, D, E, and G are nitrogen or carbon where one or more of B, D, and E is nitrogen;
with the proviso that when G=N, the group is attached to the nitrogen atom of Formula I at the four or five position of the pyrimidine ring (a and b);
X is unsaturated (= X) and is selected from:
(a) =O
(b) =$NR_5$ where $R_5$ is selected from
   (i) the group $R_4$, wherein $R_4$ is hydrogen, $C_1$–$C_4$ alkyl, hydroxy $C_1$–$C_4$ alkyl, $C_1$–$C_4$ alkanoyl, $C_3$–$C_{10}$ cycloalkyl, $C_2$–$C_6$ alkenyl, or $(CH_2)_m$-phenyl or

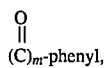
$(C)_m$-phenyl, wherein the
phenyl is unsubstituted or is substituted with from 1 to 3 substituents selected from
$C_1$–$C_4$ alkyl,
$C_1$–$C_4$ alkoxy,
$C_1$–$C_4$ alkylthio,
phenyl,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is hydrogen or a straight chain alkyl group having 1 to 4 carbon atoms;
$R_4$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with an alkyl group having from 1 to 4 carbon atoms and the N-oxides thereof; or 1- or 2-naphthyl which is unsubstituted or substituted with 1 to 3 substituents selected from
alkyl having from 1 to 4 carbon atoms and which is straight or branched, and
alkoxy having from 1 to 4 carbon atoms and which is straight or branched;
(ii) the group —$OR_x$, wherein $R_x$ is hydrogen, $R_4$, $C_1$–$C_{18}$ alkyl, $C_2$–$C_{18}$ alkenyl, $C_2$–$C_{18}$ alkynyl, or such alkyl, alkenyl or alkynyl groups substituted with $R_4$;
(iii) the group —$NR_6R_7$, wherein $R_6$ is hydrogen, $C_1$–$C_4$ alkyl, or phenyl which is unsubstituted or substituted with 1 to 3 substituents selected from straight or branched alkyl having 1 to 4 carbon atoms, straight or branched alkoxy having from 1 to 4 carbon atoms, halo, trifluoromethyl, cyano, and nitro; $R_7$ is hydrogen, $C_1$–$C_4$ alkyl, or heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with an alkyl group having from 1 to 4 carbon atoms and the N-oxides thereof; or $R_6$ and $R_7$ together with the nitrogen to which they are attached from a 4- to 7-membered ring;
(iv) or —$NHCONH_2$;
wherein X is saturated (—X), it is selected from the group $NR_3R_4$, wherein $R_4$ is as defined above, and preferably $R_3$ and $R_4$ are the same or different and are selected from p (a) hydrogen;
(b) $C_1$–$C_4$ alkyl or a cycloalkyl group having from 3 to 10 carbon atoms;
(c) when $R_3$=H, $R_4$ is $C_1$–$C_4$ alkanoyl, benzoyl, substituted benzoyl, $C_2$–$C_6$ alkenyl and those substituents previously defined for $R_5$=$R_4$;
(d) $R_3$ and $R_4$ taken together with the nitrogen atom to which they are attached to form 5- to 7-membered monocyclic heterocycles containing 1 to 4 heteroatoms, said heteroatoms being nitrogen, oxygen, or sulfur and combinations thereof, said heterocyclic group being unsubstituted or substituted with phenyl or an alkyl group having 1 to 4 carbon atoms;
wherein $R_2$ is a straight or branched hydrocarbon chain having from 1 to 20 carbon atoms and is saturated or is unsaturated and has one double bond or has two nonadjacent double bonds; and wherein $R_2$ can be bonded directly to the tetrazole ring or connected through an oxygen or sulfur atom; pharmaceutically acceptable salts and individual enantiomeric isomers and regioisomers of the compounds.

Preferred compounds of the invention include those within the following groups:

A. $R_1$ is phenyl or substituted phenyl, and $R_2$ is $C_6-C_{12}$ alkyl;

B. $R_1$ is naphthyl or substituted naphthyl, and $R_2$ is $C_6-C_{12}$ alkyl;

C. $R_1$ is 4,6-dialkoxypyrimidin-5-yl and $R_2$ is $C_6-C_{12}$ alkyl;

D. $R_1$ is 4- (2-chlorophenyl)-5,7-dimethylquinolin-2-yl, and $R_2$ is $C_6-C_{12}$ alkyl;

E. X is $-NR_3R_4$ where $R_3$ and $R_4$ independently are hydrogen, $C_1-C_4$ alkyl, $C_3-C_6$ cycloalkyl, hydroxy-$C_1-C_4$ alkyl, or $R_3$ and $R_4$ taken together with the nitrogen form pyrrolidinyl, morpholinyl, piperidinyl, thiomorpholinyl, 4-alkylpiperazinyl, or imidazolyl;

F. X is $-NR_3R_4$ where $R_3$ is hydrogen and $R_4$ is $C_1-C_4$ alkyl, $C_1-C_4$ alkanoyl, or benzoyl;

G. X is $= N-R_5$;

H. X is $= N-R_5$ where $R_5$ is hydroxy or $C_1-C_4$ alkoxy;

I. $R_1$ is 2,6-diisopropylphenyl and $R_2$ is dodecyl;

J. $R_1$ is phenyl substituted with one, two, or three $C_1-C_4$ alkyl groups;

K. X is $= N-R_5$ as the anti-isomers.

Also provided by this invention are pharmaceutical formulations comprising a compound of Formula I together with a pharmaceutically acceptable excipient, carrier, or diluent. Preferred formulations are those having any of the preferred compounds of A-K as the active ingredient. The invention also provides a method of treating hypercholesterolemia, atherosclerosis, and inhibiting the ACAT enzyme, comprising administering to a subject an effective amount of a compound of Formula I to treat such conditions and to inhibit such enzyme.

DETAILED DESCRIPTION

Pharmaceutically acceptable salts of the compounds of Formula I are also included as a part of the present invention. Suitable acids for forming salts of the compounds of Formula I containing a basic group include, but are not necessarily limited to acetic, benzoic, benzenesulfonic, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. Additional acids for use to form acid salts of the compounds of Formula I include, but are not necessarily limited to, those acids found in Tables 3 and 4 of Grant & Hackh's Chemical Dictionary, Fifth Edition, 1987:11–13. The acid addition salts are formed by procedures well known in the art.

Certain compounds of the present invention may also exist in different isomeric forms, specifically stereoisomeric forms, by virtue of the presence of asymmetric centers in the compound. The present invention contemplates all stereoisomers that may be obtained, if desired, by methods known in the art as, for example, the separation of stereoisomers by chiral chromatographic coles. The compounds wherein X is $= N-R^5$ can exist as syn and anti-isomers. While the anti is preferred, the invention includes the pure syn as well as mixtures thereof.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

In Formula I, $R_2$, which can be at the 1 or 2 position of the tetazole ring, can be $C_1-C_{20}$ alkyl, $C_1-C_{20}$ alkoxy, or $C_1-C_{20}$ alkylthio. Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups. Any of these groups can be attached to the tetrazole ring through oxygen or sulfur.

$R_2$ can also be an alkenyl group, an alkenyloxy, or alkenylthio. Illustrative examples of straight or branched hydrocarbon chains having from 1 to 20 carbon atoms and having one double bond or two nonadjacent double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl. Any of these groups can be attached to the tetrazole ring through oxygen or sulfur.

$R_1$ in Formula I includes $C_1-C_4$ alkoxy and $C_1-C_4$ alkylthio. Straight or branched alkoxy groups having 1 to 4 carbon atoms include methoxy, ethoxy, n-propoxy, n-butoxy, and isopropoxy. $C_1-C_4$ alkylthio includes groups such as methylthio, ethylthio, isopropylthio, and the like.

Straight or branched alkyl groups having from 1 to 4 carbon atoms include, for example, methyl, ethyl, n-propyl, isopropyl, t-butyl, and n-butyl. Hydroxy-$C_1-C_4$ alkyl groups include hydromethyl, 2-hydroxyethyl, 2-hydroxypropyl, and 4-hydroxybutyl. $C_1-C_4$ alkanoyl groups include formyl, acetyl, and propianyl. $C_2-C_6$ alkenyl includes 2-propenyl, 3-butenyl, 2-hepenyl, and the like.

Cycloalkyl groups having from 3 to 10 carbon atoms which $R_1$ and $R_4$ may represent include cyclopropyl, cyclobutyl, cyclopentyl, cyclohexyl, cycloheptyl, and cyclooctyl.

Halo is fluoro, chloro, bromo, or iodo, but preferably bromo and chloro. Benzoyl is CO phenyl, and substitued benzoyl is CO phenyl where the phenyl is substitued with from 1 to 3 substituents as defined above. Typical substituted benzoyl include 2-chlorobenzoyl, 4-ethylbenzoyl, 3-nitrobenzoyl, 3-nitrobenzoyl, and the like.

A 5- or 6-membered monocyclic or fused bicyclic heterocycle is a monocyclic or fused bicyclic aromatic ring containing at least one to four heteroatoms in at least one ring, such as nitrogen, oxygen, or sulfur, or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycles containing a nitrogen atom.

More specifically, such a heterocycle may be a 2-or 3-thienyl; 2-or 3-furanyl; 2-, 3-, or 4-pyridyl or 2-, 3-, or 4-pyridinyl-N-oxide; 2-, 4-, or 5-pyrimidinyl; 3- or 4-pyridazinyl; 2-pyrazinyl; 2-pyrazinyl-N-oxide; 2-or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3-or 5-(1,2,4)triazolyl; 4-or 5-(1,2,3)-triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

$R_x$ includes $C_1$–$C_{18}$ alkyl, $C_2$–$C_{18}$ alkenyl, $C_2$–$C_{18}$ alkynyl, and such alkyl, alkenyl, and alkynyl group substituted with $R_4$. The term "$C_1$–$C_{18}$ alkyl" is included within $C_1$–$C_{20}$ alkyl, namely a straight or branched carbon chain having from 1 to 18 carbons. $C_2$–$C_{18}$ alkenyl are straight or branched chains having from 2 to 18 carbons and one double bond or two nonadjacent double bonds. $C_2$–$C_{18}$ alkynyl groups have from 2 to 18 carbons and one triple bond or two nonadjacent triple bonds. Any of these alkyl, alkenyl, and alkynyl groups can be substituted with $R_4$, for example to give groups such as alkylphenyl, alkenylphenyl, alkynylphenyl, alkyl-heteroaryl, alkylnaphthyl, and the like. Such groups are well known in the art, for instance as described in EP 0570245 which is incorporated herein by reference for its teaching of various substituted oximes.

Preferred compounds of this invention are defined by Formula I wherein $R_1$ is phenyl or substituted phenyl, and X is —$NR_3R_4$. Such compounds have the formula

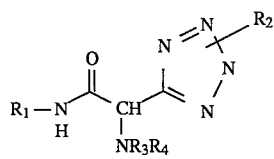

wherein $R_1$ is phenyl or substituted phenyl as defined above, and $R_2$, R3, and $R_4$ are as defined above. Typical compounds falling within this class include the following:

| $R_1$ | $R_2$ | $R_3$ | $R_4$ |
| --- | --- | --- | --- |
| phenyl | isopentyl | methyl | ethyl |
| 3-methoxyphenyl | n-hexyl | H | isopropyl |
| 3,4-dichlorophenyl | n-octyl | cyclopropyl | methyl |
| 2-methylthiophenyl- | 1,1-dimethyl-heptyl | H | 2-hydroxyethyl |
| 2-ethylphenyl | thiomethyl | H | propionyl |
| 2-cyano-4-trifluoromethylphenyl | | | |
| 2-ethoxycarbonyl-phenyl-4-chloro-6-methylphenyl | 3-hexenyl | | |
| 3-nitrophenyl | 1,1-dimethyl-5-heptenyl | | |
| 2,6-diisobutyl-phenyl | n-octyl | | |
| 2,4-dinitrophenyl | n-heptyl | H | acetyl |
| 2-aminomethylphenyl | n-undodecyl | ethyl | methyl |

Another class of preferred compounds defined by Formula I have the formula

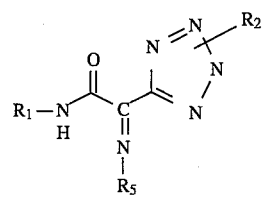

wherein $R_1$ is phenyl or substituted phenyl and $R_2$ and $R_5$ are as defined above. Examples of such compounds include the following:

| $R_1$ | $R_2$ | $R_5$ |
| --- | --- | --- |
| phenyl | n-pentyl | methoxy |
| 2-methylphenyl | n-octyl | hydroxy |
| 2,6-dichlorophenyl | 3-decenyloxy | isopropoxy |
| 2-cyano-4-fluorophenyl | 1,2-dimethyloctyl | n-butoxy |
| 3-nitro-4-carboxyphenyl | isooctylthio | methyl |
| 3,5-diethylphenyl | n-nonyl | phenyl |
| 3,5-dibromophenyl | 5-(5-butyl)decyl | 3-hydroxyphenyl |
| 2-ethylthiophenyl | 4-t-butyl-4-isopropyldecyl | 3-chlorophenyl |
| 2,6-difluorophenyl | 3-n-pentyl-4-n-butyloctyloxy | 4-nitrophenyl-methyl |
| 3-methoxyphenyl | 3,5-octadienyl | aminocarbonyl-amino |
| 3,4-diethylphenyl | 4-decenylthio | phenylamino |

Another class of preferred compounds have the general formula

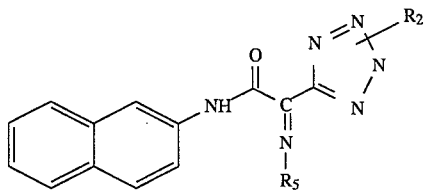

wherein $R_2$ and $R_5$ are as defined above, and the naphthyl group can be substituted.

Other compounds of the invention have the formula

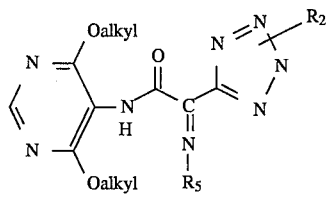

wherein $R_2$ and $R_5$ are as defined above. Typical compounds within this group include

| alkyl | $R_2$ | $R_5$ |
| --- | --- | --- |
| methyl | n-decyl | ethoxy |
| ethyl | n-butyl | isopropoxy |
| isopropyl | 1-methyloctyl | phenyl |
| n-butyl | 1,1-dimethyldecyl | 3-chlorophenyl |

Still other compounds of the invention have the formula

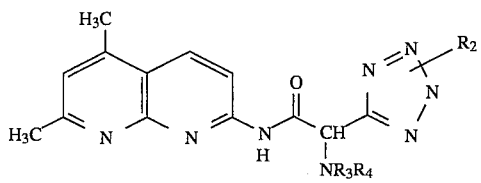

wherein $R_2$, R3, and $R_4$ are defined above. Closely related to those of the above formula are compounds defined by the formula

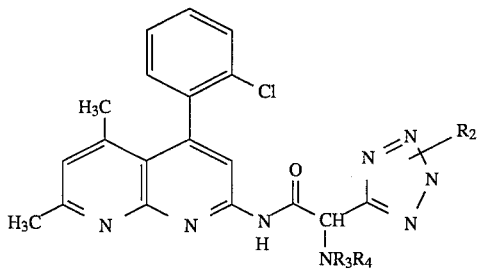

wherein $R_2$, $R_3$, and $R_4$ are as defined above.

Of particular importance are compounds of the above formula where

| $R_2$ | $R_3$ | $R_4$ |
|---|---|---|
| n-decyl | methyl | ethyl |
| n-octyl | methyl | ethyl |
| n-undecyl | H | 3-chlorophenyl |
| 1,1-dimethyl-heptyloxy | | ⟨cyclopentyl⟩ |
| 1-methyloct-3-enyl | | ⟨morpholinyl⟩ |

Still other compounds of the invention have the formula

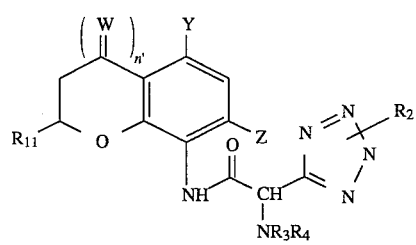

wherein $R_2$, $R_3$, $R_4$, $R_{11}$, W, n', Y, and Z are as defined above.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, Biochemica et Biophysica Acta, 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rat liver microsomes (designated LAI).

These data appear in Table 1 where they are expressed as $IC_{50}$ values; i.e., the concentration of test compound required to inhibit the activity of the enzyme by 50%.

In one in vivo screen designated APCC, male Sprague-Dawley rats (200–225 g body weight) were randomly divided into treatment groups and dosed at 4 PM with either vehicle (CMC/Tween) or suspensions of invention compounds in vehicle. The normal chow diet was then replaced with a high fat, high cholesterol diet (5.5% peanut oil, 1.5% cholesterol, and 0.5% cholic acid). The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention also appear in Table I as the percent change in total cholesterol (%TC) from control animals given vehicle and diet only. All compounds in the APCC test reported in Table 1 were administered by garage at 30 mg/kg.

TABLE 1

| Compound of Example | LAI ($IC_{50}$, μM) | APCC (% change in TC) |
|---|---|---|
| 1 | 0.012 | −56 |
| 2 | 0.018 | −57 |
| 3 | 0.015 | −47 |
| 4 | 0.009 | −59 |
| 5 | 0.215 | −46 |
| 6 | 0.086 | −51 |
| 7 | 0.032 | −28 |
| 8 | 0.390 | −11 |
| 9 | 0.040 | −40 |
| 10 | 0.094 | −51 |
| 11 | 0.135 | −50 |
| 12 | 0.029 | |
| 13 | 0.002 | −43 |
| 14 | 0.040 | −19 |
| 15 | 0.028 | −70 |
| 16 | 0.003 | −67 |
| 17 | 0.040 | −67 |
| 18 | 0.222 | −20 |
| 23 | 0.002 | −74 |
| 24 | 0.049 | −31 |
| 27 | 0.51 | |
| 28 | 0.15 | −18 |
| 29 | 0.043 | −70 |
| 32 | >1 | −9 |
| 36 | 0.212 | |
| 41 | 0.025 | −65 |

In therapeutic use as agents for treating hypercholesterolemia or atherosclerosis, the compounds of Formula I or pharmaceutically acceptable salts thereof are administered to the patient at a dosage which is effective in inhibiting ACAT. Such ACAT-inhibiting levels generally are from about 50 to about 3000 mg per day, ideally from about 100 to about 1000 mg per day. For a normal human adult of approximately 70 kg of body weight, a typical dosage of from about 1 to about 40 mg/kg of body weight per day will be utilized. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner cachets are also included.

Tablets, powders, cachets, and capsules can be used as solid dosage forms suitable for oral administration. Sustained-release formulation can be prepared utilizing conventional techniques such as polymers, osmotic pumps, wax, and the like.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention can be prepared by various routes., all of which are generally known in the art. The compounds in Formula I wherein X has a saturated carbon/nitrogen bond and is a primary, secondary, or tertiary amine, and $R_1$ and $R_2$ are as defined above, are prepared as set forth in Chart I hereof. Namely, a 2-bromo-2-(tetrazolyl)-acetamide can be reacted with an amine via a halo displacement reaction to give the substituted amines of the invention. The general reaction is depicted

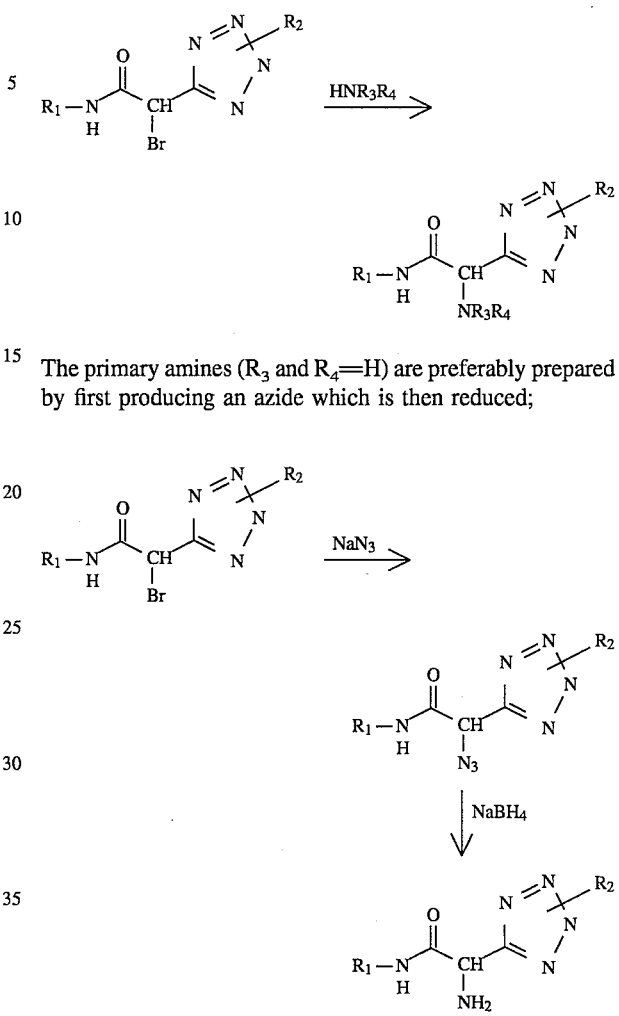

The primary amines ($R_3$ and $R_4$=H) are preferably prepared by first producing an azide which is then reduced;

In all of the foregoing, $R_1$, $R_2$, $R_3$, and $R_4$ are as defined above. The primary amines can be alkylated and acylated by standard procedures to provide compounds wherein $R_3$ and $R_4$ are other than hydrogen.

In Chart I, the tetrazole ester (2) is synthesized via treatment of ethylcyanoacetate (1) with tributyltin azide. Alkylation of the tetrazole ester (2) with a halide of the formula $R_2$-halo wherein $R_2$ has the meaning defined in Formula I and halo is, e.g., bromine or chlorine, provides a mixture of (3) and (4), i.e., the 2- and 1-regioisomers, respectively, isomers which are separable by chromatography. Esters (3) and (4) can then be independently hydrolyzed to the acids (5, 9), which are brominated in refluxing carbon tetrachloride to give compounds (6) and (10). The acids (6, 10) are coupled with an amine of the formula $R_1NH_2$ wherein $R_1$ has the meaning defined in Formula I using dicyclohexylcarbodiimide (DCC) in dichloromethane to give the 2- and 1-substituted tetrazole amides (7) and (11), respectively. The α-bromotetrazole amides (7, 11 ) undergo nucleophilic displacement to α-substituted aminotetrazoles (8, 12) when treated with cyclic and acyclic secondary amines (i.e., with $R_3$ and $R_4$ as previously defined in Formula I) in refluxing THF or ethanol. Compounds of formula (8) and (12) wherein $R_3$=$R_4$=H are also prepared from intermediates (7) and (11) by treatment with sodium azide in ethanol followed by reduction of the azide (13) with sodium borohydride or other reducing agent.

An alternative means of preparing saturated amines of Formula I with X=NR$_3$R$_4$, wherein R$_3$=H and R$_4$=R$_5$, is set forth in Chart II.

In Chart II, the tetrazole acetic acids (5, 9) are independently coupled with an amine of the formula R$_1$NH$_2$, wherein R$_1$ has the meaning defined in Formula I, using dicyclohexylcarbodiimide (DCC) in dichloromethane to give the appropriately substituted amides (14, 18). Compounds of formulas (14) and (18) undergo oxidation to α-ketoamides (15, 19) in the presence of selenium dioxide in refluxing aqueous dioxane. Treatment of the ketoamides (15, 19) with an amine of the formula R$_5$NH$_2$ and pyridine in refluxing ethanol gives the imines (16 or 20, 20, R$_5$=R$_4$), which are converted to the corresponding amines (17, 21) upon treatment with sodium borohydride or a similar reducing agent.

The compounds of Formula I wherein X is unsaturated, and has a carbon/oxygen double bond or a carbon/nitrogen double bond, i.e., = N—R$_5$, wherein R$_5$ is selected from substituents previously defined in Formula I, are also prepared from the α-ketoamides, i.e., intermediates (15, 19) set forth in Chart II.

Oximes (R$_5$=OH) are synthesized by treating an ethanolic solution of an α-ketoamide (15 or 19) with pyridine and hydroxylamine hydrochloride. The solution is refluxed for approximately 45 minutes, cooled, and after work-up yields the corresponding oxime (16 and 20 where R$_5$=OH). Employing similar reaction conditions, only substituting the appropriate amount of hydrazine (R$_6$R$_7$NNH$_2$) for that of hydroxylamine hydrochloride, gives hydrazones of formula (16 and 20, R$_5$=R$_6$R$_7$N), where R$_6$ and R$_7$ have been previously defined in Formula I. For semicarbazones, the ketone (15 or 19) is dissolved in aqueous ethanol and treated with semicarbazide hydrochloride and sodium acetate. The solution is refluxed for 1 hour, cooled to 0° C., and the semicarbazone (16 or 20, R$_5$=R$_6$=NHCONH$_2$) is collected by filtration and recrystallized from a suitable solvent such as aqueous ethanol.

The compounds in Formula I bearing O-alkylated oximes (R$_5$=ORx), wherein OR$_x$ is selected from substituents previously defined in Formula I, can be prepared as set forth in Chart III hereof.

In Chart III, ethyl cyanoglyoxylate-2-oxime (22) is treated with sodium hydride in THF at 0° C., followed by the addition of a halide of the formula R$_x$ halo, wherein R$_x$ has the meaning defined in Formula I and halo is preferably bromine, chlorine, or iodine, to give the oxime ether (23). The tetrazole ester (24) is synthesized via treatment of (23) with α-tributyltin azide in refluxing p-dioxane, followed by crystallization of (24) from ethereal HCl. Alkylation of the tetrazole ester (24) with a halide of the formula R$_2$ halo, wherein R$_2$ and halo have been previously defined, provides a mixture of (25) and (26), the 2- and 1-regioisomers respectively, isomers which are separable by chromatography. The tetrazole ester (e.g., 25) is hydrolyzed to the corresponding acid (e.g., 27) which is coupled with an amine of the formula R$_1$NH$_2$, wherein R$_1$ has the meaning defined in Formula I, using DCC in dichloromethane to give compounds of formula (28) as a mixture of E- and Z-isomers, isomers which are separable by chromatography.

(R$_1$, R$_2$, R$_3$, and R$_4$ as defined in Formula I)

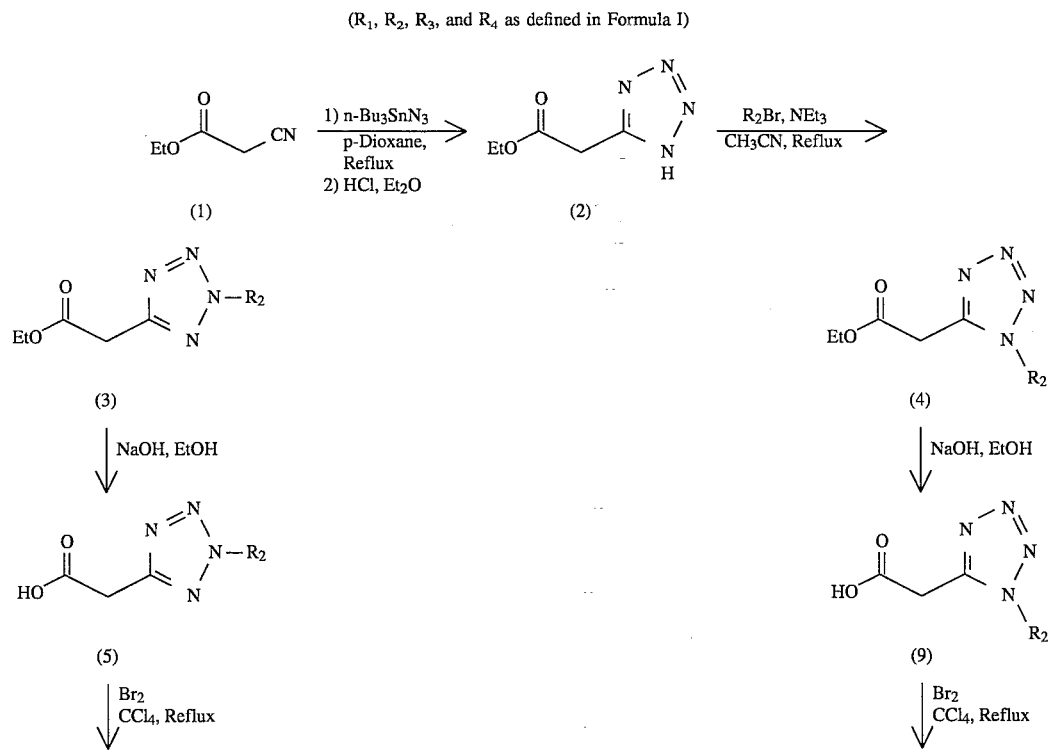

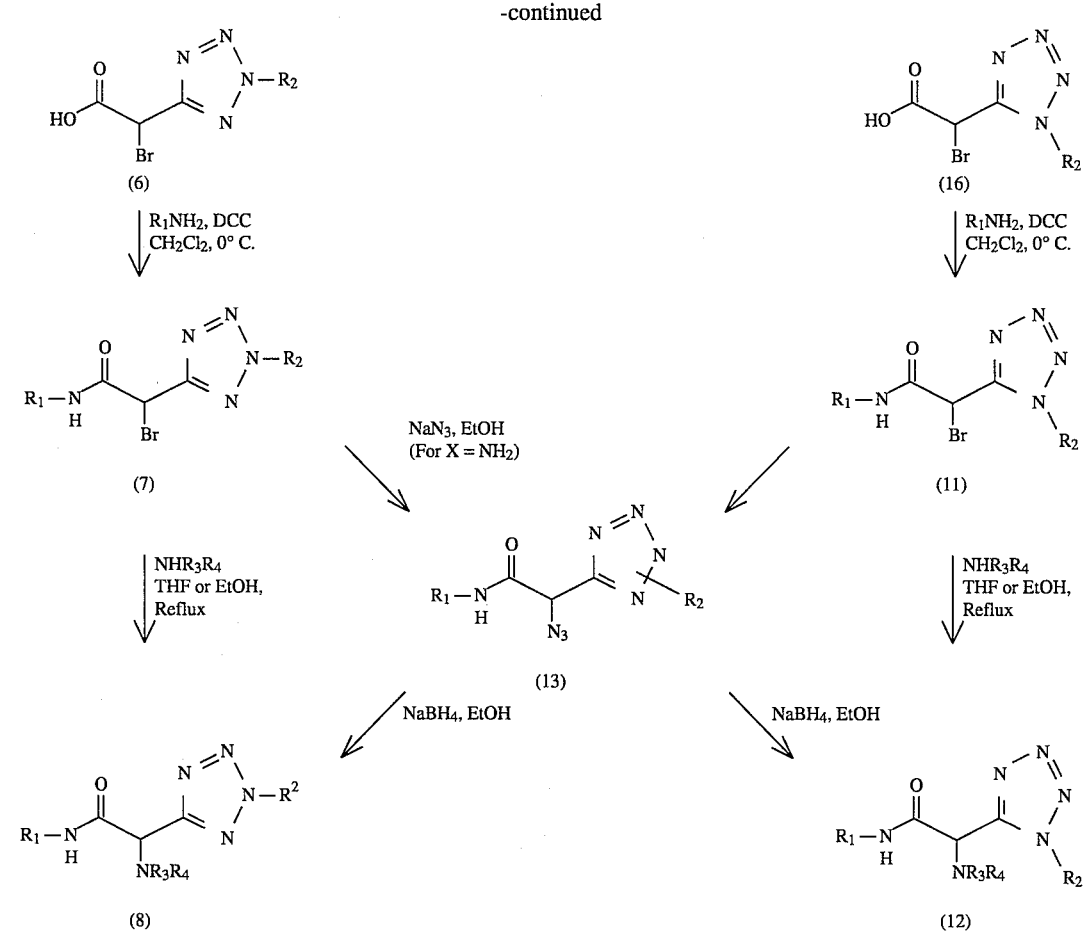
CHART II
($R_1$, $R_2$, $R_3$, and $R_4$ as defined in Formula I)
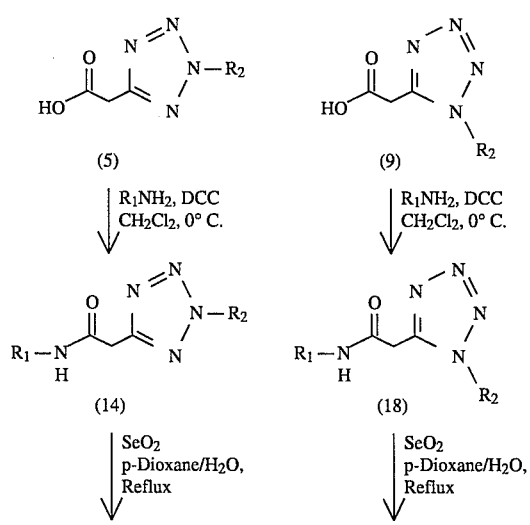
-continued
CHART II
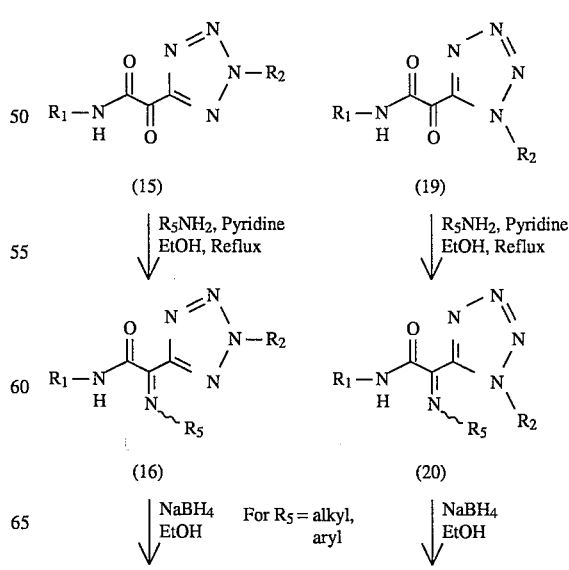
For $R_5$ = alkyl, aryl -continued
CHART II

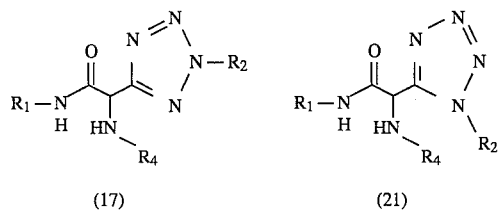

(17)    (21)

CHART III ($R_1$ and $R_2$ as defined in Formula I)

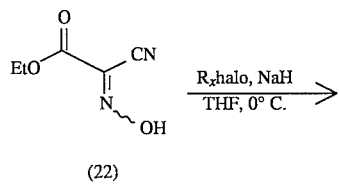

(22)

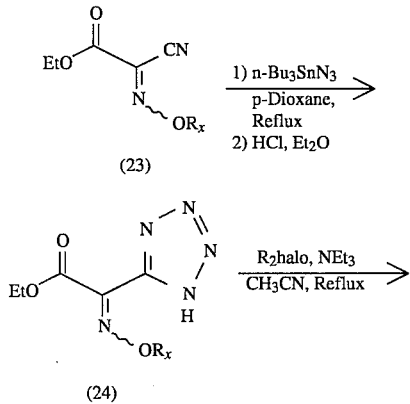

(23)

(24)

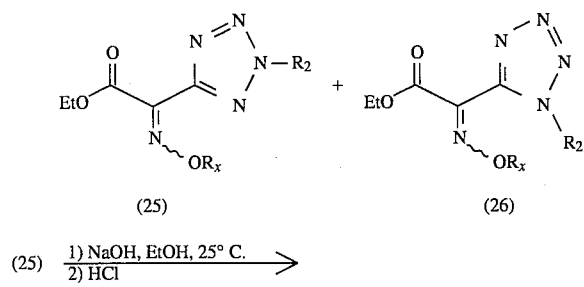

(25)    (26)

(25) $\xrightarrow{\text{1) NaOH, EtOH, 25° C.}}{\text{2) HCl}}$

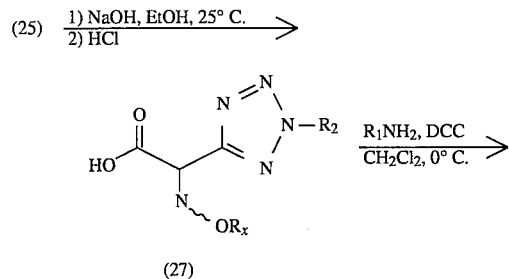

(27)

-continued
CHART III

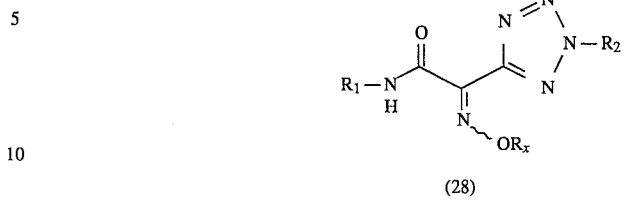

(28)

The practice of the present invention is further illustrated by the following detailed examples, none of which are to be construed as limiting the invention in any respect.

EXAMPLE 1

(±)-N-(2,6-diisopropylphenyl)-2-(2-dodecyl-2H-tetrazol-5-yl)-2-thiomorpholin-4-yl-acetamide (a) Tetrazoleacetic acid, ethyl ester Ethyl cyanoacetate (50 g, 0.44 mol) was added in one portion to a solution containing α-tributyltin azide (176 g, 0.53 mol) and p-dioxane (250 mL). The solution was heated at reflux overnight, cooled to 24° C., and the solvent was concentrated in vacuo leaving a viscous liquid. The liquid was dissolved in diethyl ether (1.5 L) and gaseous hydrogen chloride was bubbled into the solution over 20 minutes. The precipitate was collected by filtration and thoroughly washed with diethyl ether to give tetrazoleacetic acid, ethyl ester (59.2 g, 69%) as the HCl salt.

(b) 2-Dodecyltetrazoleacetic acid, ethyl ester

The tetrazoleacetic acid, ethyl ester (50 g, 0.26 tool) obtained in (a) was suspended in acetonitrile (600 mL) and triethylamine (52.4 g, 0.52 tool)was added in one portion. The solution was heated at reflux for 5 minutes, cooled to 24° C., and then treated dropwise with 1-bromododecane (64.5 g, 0.26 mol). The solution was refluxed overnight, cooled, and the solvent concentrated in vacuo. The residue was triturated with ethyl acetate (300 mL), filtered, and the filtrate was washed with aqueous HCl (1M), brine, dried ($MgSO_4$), and filtered. The filtrate was concentrated in vacuo leaving a viscous liquid. The 2-isomer was separated from the crude mixture using silica gel chromatography (elution with 25% EtOAc/75% hexane), isolating 2-dodecyltetrazoleacetic acid, ethyl ester (41.8 g, 49%) as a pale yellow liquid.

(c) 2-Dodecyltetrazoleacetic acid

To a solution of 2-dodecyltetrazoleacetic acid ethyl ester (5.1 g, 15.7 mmol) in ethanol (60 mL) were added sodium hydroxide pellets (1.25 g, 31.4 mmol) in one portion. The solution was stirred overnight at room temperature. The solution was concentrated in vacuo and the residue was dissolved in water. The aqueous solution was acidified (pH=1.0) with concentrated HCl and the product was extracted with one portion of ethyl acetate (150 mL). The organic solution was washed with brine, dried ($MgSO_4$), filtered, and concentrated in vacuo to give 4.7 g (99%) of a wax-like solid identified as 2-dodecyltetrazoleacetic acid, mp 70°–72° C.

(d) α-Bromo-2-dodecyltetrazoleacetic acid

The 2-dodecyltetrazoleacetic acid (4.7 g, 15.8 mmol) was suspended in carbon tetrachloride (5 mL) and warmed to 45° C. The solution was diluted by dropwise addition of bromine (2.6 g, 16.3 mmol), and the mixture was further heated to reflux with stirring for 5 hours. The solution was cooled to room temperature, diluted with 50 mL of ethyl acetate, washed with brine, dried (MgSO$_4$), and filtered. The filtrate was concentrated in vacuo to give α-bromo-2-dodecyltetrazoleacetic acid (5.3 g, 86%) as an orange colored liquid;

$^1$H NMR (CDCl$_3$): δ5.8 (s, 1H), 4.6 (t, 2H), 2.0 (m, 2H), 1.3 (s, 18H), 0.9 (t, 3H) ppm.

(e) (±)-N-(2,6-diisopropylphenyl)-2-(2-dodecyl-2H-tetrazol-5-yl)-2-bromoacetamide To a solution of α-bromo-2-dodecyltetrazoleacetic acid (5.0 g, 13.3 mmol) in dichloromethane (75 mL), cooled to −10° C., were added 2,6-diisopropylaniline (2.3 g, 12.9 mmol) and DCC (2.7 g, 13 mmol), respectively. The suspension was gradually warmed to room temperature and was stirred for 12 hours. The mixture was filtered and the filtrate was concentrated in vacuo leaving a yellow liquid. The crude product was purified using silica gel chromatography (elution with 10% ethyl acetate/90% hexane) to give (±)-N-(2,6-diisopropylphenyl) -2-(2-dodecyl-2H-tetrazol-5-yl)-2-bromo-acetamide ( 4.8 g, 65% ) as a colorless liquid which crystallized on standing;

$^1$H NMR (CDCl$_3$): δ 8.4 (bs, 1H), 7.3 (t, 1H), 7.2 (d, H), 5.8 (s, 1H), 4.6 (t, 2H), 3.1 (m, 2H), 2.0 (m, 2H), 1.3 (bs, 4H), 1.2 (s, 14H), 1.1 (m, 12H), 0.9 (t, 3H) ppm.

(f) (±)-N-(2,6-diisopropylphenyl)-2-(2-dodecyl-2H -tetrazol-5-yl -2-thiomorpholin-4-yl-acetamide To a solution of thiomorpholine (0.38 g, 3.7 retool) in THF (10 mL) was added the α-bromoamide obtained from (e) (1 g, 1.87 mmol) in a single portion. The solution was refluxed for 4 hours, cooled to room temperature, and stirred for 36 hours. The precipitate which had formed was filtered and the filtrate was concentrated in vacuo leaving a white solid. The white solid was purified using silica gel chromatography (elution with 25% ethyl acetate/hexane) to give (±)-N-(2,6-diisopropylphenyl ) -2-(2-dodecyl-2H-tetrazol-5-yl) -2-thiomorpholin-4-yl-acetamide ( 0.79 g, 7 6% ), mp 97°–98 ° C.

Following the general procedure for Example 1, the following compounds were obtained by substituting a different amine for thiomorpholine in the example above.

EXAMPLE 2

(±)-N-(2,6-Diisopropylphenyl)-2-(2-dodecyl-2H-tetrazol -5-yl)-2-morpholino-4-yl-acetamide, mp 82°–83° C.

EXAMPLE 3

(±)-N-(2,6-Diisopropylphenyl)-2-(2-dodecyl-2H-tetrazol -5-yl)-2-piperidin-1-yl-acetamide, mp 60°–62° C.

EXAMPLE 4

(±) -N-(2,6-Diisopropylphenyl)-2-(2-dodecyl-2H-tetrazol -5-yl ) -2-pyrrolidinyl-1-yl-acetamide $^1$H NMR (CDCl$_3$): δ 8.7 (bs, 1H), 7.3 (m, 1H), 7.2 (d, 2H), 4.7 (s, 1H), 4.6 (t, 2H), 3.1 (m, 2H), 2.8 (m, 2H), 2.6 (m, 2H), 2.0 (m, 2H), 1.8 (bs, 4H), 1.4 (bs, 4H), 1.3 (s, 14H), 1.2 (dd, 12H), 0.9 (t, 3H) ppm.

EXAMPLE 5

(±)-N-( 2,6-Diisopropylphenyl)-2-( 2-dodecyl-2H-tetrazol -5-yl ) -2-imidazol-1-yl-acetamide $^1$H NMR (CDCl$_3$): δ 7.8 (s, 1H), 7.5 (s, 1H), 7.4 (s, 1H), 7.3 (m, 1H), 7.2 (s, 1H), 7.1 (d, 2H), 6.5 (s, 1H), 4.7 (t, 2H), 2.8 (m, 2H), 2.0 (m, 2H), 1.4 (bs, 4H), 1.3 (s, 14H), 1.2 (m, 12H), 0.9 (t, 3H) ppm.

When in the procedure of Example 1 (f), an appropriate amount of ethanol was substituted for THF and the general procedure of Example 1 (f) was followed, the following compounds were obtained substituting the amines below for thiomorpholine.

EXAMPLE 6

(±)-N-(2,6-Diisopropylphenyl)-2-(2-dodecyl-2-tetrazol -5-yl)-2-(4-methyl-piperazin-1-yl)-acetamide $^1$H NMR (CDCl$_3$): δ 8.8 (s, 1H), 7.3 (m, 1H), 7.2 (d, 2H), 4.8 (s, 1H), 4.6 (t, 2H), 3.1 (m, 2H), 2.7 (m, 4H), 2.6 (m, 4H), 2.3 (s, 3H), 2.0 (m, 2H), 1.4 (bs, 4H), 1.3 (s, 14H), 1.2 (m, 12H), 0.9 (t, 3H)ppm.

EXAMPLE 7

(±)-2-Diethylamino-N-(2,6-diisopropylphenyl) -2-(2-dodecyl-2H-tetrazol-5-yl)-acetamide $^1$H NMR (CDCl$_3$): δ 9.0 (s, 1H), 7.3 (m, 1H), 7.2 (d, 2H), 5.1 (s, 1H), 4.6 (t, 2H), 3.1 (m, 2H), 2.9 (m, 2H), 2.4 (m, 2H), 2.0 (m, 2H), 1.4 (bs, 4H), 1.3 (s, 4H), 1.2 (m, 12H), 0.9 (t, 3H) ppm.

EXAMPLE 8

(±)-2-[Bis-(2-hydroxyethyl)-amino]-N-(2,6-diisopropylphenyl) -2-(2-dodecyl-2H-tetrazol-5-yl)-acetamide $^1$H NMR (CDCl$_3$): δ 9.3 (s, 1H), 7.3 (m, 1H), 7.2 (d, 2H), 5.1 (s, 1H), 4.6 (t, 2H), 3.8 (m, 2H), 3.7 (m, 2H), 3.1 (m, 6H), 2.7 (d, 2H), 2.0 (m, 2H), 1.4 (bs, 4H), 1.3 (s, 14H), 1.2 (d, 12H), 0.9 (t, 3H) ppm.

EXAMPLE 9

(±)-N-(2,6-Diisopropylphenyl)-2-dimethylamino -(2-dodecyl-2H-tetrazol-5-yl)-acetamide $^1$H NMR (CDCl$_3$): δ 8.8 (bs, 1H), 7.3 (m, 1H), 7.2 (d, 2H), 4.7 (bs, 1H), 4.6 (t, 2H), 3.1 (m, 2H), 2.4 (bs, 6H), 2.0 (m, 2H), 1.4 (bs, 4H), 1.3 (s, 14H), 1.2 (dd, 12H), 0.9 (t, 3H) ppm.

EXAMPLE 10

(±)-2-Amino-N-(2,6-diisopropylphenyl)-2-(2-dodecyl -2H-tetrazol-5-yl)-acetamide (±)-N-(2,6-diisopropylphenyl)-2-(2-dodecyl -2H-tetrazol-5-yl)-2-bromoacetamide (1 g, 1.87 mmol) from Example 1 (e) was added to a solution containing sodium azide (0.24 g, 3.7 mmol) in ethanol (20 mL). The solution was stirred for 72 hours at 24° C. Sodium borohydride (0.07 g, 1.87 mmol) was added to the reaction mixture in one portion. The suspension was stirred for 12 hours at 24° C., then concentrated in vacuo. The resulting residue was triturated with ethyl acetate, filtered, and the filtrate was concentrated in vacuo leaving a viscous liquid. The liquid was dissolved in 10 mL of 50% ethyl acetate/ 50% hexane and purified by silica gel chromatography (elution with 50% ethyl acetate/50% hexane) to give (±)-2-amino-N-(2,6-diisopropylphenyl)-2-(2-dodecyl -2H-tetrazol-5-yl)-acetamide (0.58 g, 66%) as a colorless liquid;

$^1$H NMR (CDCl$_3$): δ 8.7 (s, 1H), 7.3 (m, 1H), 7.2 (d, 2H), 5.2 (s, 1H), 4.6 (t, 2H), 3.0 (m, 2H), 2.4 (bs, 2H), 2.0 (m, 2H), 1.4 (bs, 4H), 1.3 (s, 14H), 1.2 (dd, 12H), 0.9 (t, 3H) ppm.

EXAMPLE 11

N-(2,6-diisopropylphenyl)-2-(2-dodecyl-2H-tetrazol -5-yl)-2-oxo-acetamide

Selenium dioxide (1.38 g, 12.4 mmol) was added to a solution of p-dioxane/water (10 g, 0.3 g) and warmed on a steam bath until dissolution occurred. The solution was cooled to 24° C., followed by the addition of N-(2,6-diisopropylphenyl)-2-(2-dodecyl)-2H-tetrazol -5-yl)-acetamide (4.5 g, 9.87 mmol) in one portion. The solution was heated to reflux and stirred for 3 hours. After cooling, the black precipitate was filtered and washed with ethyl acetate. The filtrate was concentrated in vacuo and the resulting liquid was dissolved in 10 mL of 25% ethyl acetate/75% hexane and purified using silica gel chromatography (elution with 25% ethyl acetate/75% hexane). The product, N-(2,6-diisopropylphenyl)-2-(2-dodecyl-2H-tetrazol -5-yl)-2-oxo-acetamide, was isolated as a viscous yellow liquid (3.6 g, 77%) which gradually solidified on standing, mp 65–67° C.

EXAMPLE 12

N-(2,6-diisopropylphenyl)-2-(2-dodecyl-2H-tetrazol -5-yl)-2-hydroxyimino-acetamide The α-ketoamide from Example 11 (0.32 g, 0.7 mmol) was dissolved in ethanol (2 mL) and treated with hydroxylamine hydrochloride (0.32 g, 4.6 mmol) and pyridine (2 mL), respectively. The mixture was refluxed on a steam bath for 45 minutes, cooled to room temperature, and concentrated in vacuo. The resulting liquid was dissolved in 50 mL ethyl acetate and washed with aqueous HCl (1 M), brine, dried (Na$_2$SO$_4$), and filtered. The filtrate was concentrated in vacuo leaving a viscous liquid that was purified using silica gel chromatography (elution with 25% ethyl acetate/ 75% hexane). Fractions containing the product were combined and concentrated in vacuo to give N-(2,6-diisopropylphenyl)-2-(2-dodecyl-2H-tetrazol -5-yl)-2-hydroxyamino-acetamide (0.28 g, 85%) as a colorless viscous liquid;

$^1$H NMR (CDCl$_3$): δ 8.3 (bs, 1H), 7.4 (t, 1H), 7.2 (m, 2H), 4.7 (t, 2H), 3.0 (m, 2H), 2.1 (m, 2H), 1.6 (bs, 1H), 1.4 (bs, 4H), 1.3 (s, 14H), 1.2 (m, 12H), 0.9 (t, 3H) ppm.

EXAMPLE 13

E-N-(2,6-Diisopropylphenyl)-2-(2-dodecyl-2H-tetrazol -5-yl)-2-methoxyimino-acetamide (a) To a cooled (0°) solution of ethyl cyanoglyoxylate-2-oxime (35.9 g, 0.25 tool) in THF (250 mL), was added sodium hydride (10.5 g, 0.26 tool) in small portions under a nitrogen atmosphere. The mixture was stirred for 10 minutes, followed by the dropwise addition of iodomethane (52 g, 0.36 mol). The suspension gradually warmed to 24° C. and was stirred 12 hours. Ethyl acetate (200 mL) and 50 mL aqueous hydrochloric acid (1 M) were added. The layers were separated, and the organic phase was washed with brine, dried (MgSO$_4$), and filtered. The filtrate was concentrated in vacuo leaving a maroon colored liquid that was purified using silica gel chromatography (elution with 25% ethyl acetate/75% hexane) to give ethyl cyano-2-methoxyiminoglyoxylate (27.1 g, 56%) as a colorless liquid;

$^1$H NMR (CDCl$_3$): δ 4.4 (q, 2H), 4.3 (s, 3H), 1.4 (t, 3H) ppm.

(b) Ethyl cyano-2-methoxyimino-glyoxylate from (a) (25 g, 0.15 tool) was added to a solution containing n-tributyltin azide (19.5 g, 0.15 tool) and p-dioxane (100 mL). The solution was refluxed for 12 hours, cooled to room temperature, and the solvent was concentrated in vacuo. The resulting viscous syrup was dissolved in ethyl ether and treated with gaseous HCl for about 30 minutes. The ethereal HCl was concentrated in vacuo and the residue was triturated with hexane, and the solid was collected by filtration. The solid was thoroughly washed with hexane and dried at 60° C. to give ethyl-2-methoxyimino-2-(1H-tetrazol -5-yl)-acetate (22.3 g, 97%) as a white solid;

$^1$H NMR (CDCl$_3$): δ 4.5 (q, 2H), 4.4 (s, 3H), 1.4 (t, 3H) ppm.

(c) The tetrazole from (b) (21 g, 0.10 tool) was dissolved in acetonitrile (250 mL) and diluted by addition of triethylamine (11.1 g, 0.11 tool) in one portion. The solution was heated at reflux for 10 minutes, cooled to room temperature, followed by the dropwise addition of 1-bromododecane (27.4 g, 0.11 mol). The solution was reheated to reflux and stirred overnight. After cooling to room temperature, the acetonitrile was concentrated in vacuo and the residue was triturated with ethyl acetate and filtered. The filtrate was washed with brine, dried (MgSO$_4$), filtered, and the filtrate was concentrated in vacuo. The regioisomers were separated by silica gel chromatography (elution with 20% ethyl acetate/ 80% hexane) to give 20.2 g of 2-(2-dodecyl-2H-tetrazol -5-yl)-2-methoxyimino-acetic acid, ethyl ester (52%) as a viscous liquid and 9.1 g of 2-(1-dodecyl-1H-tetrazol -5-yl)-2-methoxyimino-acetic acid, ethyl ester (23%) as a white solid;

$^1$H NMR (CDCl$_3$, 2-isomer): δ 4.7 (t, 2H), 4.4 (q, 2H), 4.2 (s, 3H), 2.0 (m, 2H), 1.4 (m, 6H), 1.2 (s, 14H), 0.9 (t, 3H) ppm. For the 1-isomer: δ 4.4 (q, 2H), 4.2 (t, 2H), 4.25 (s, 3H), 1.9 (m, 2H), 1.4 (m, 6H), 1.2 (s, 14H), 0.9 (t, 3H) ppm.

(d) The 2-(2-dodecyl-2H-tetrazol-5-yl)-2-methoxyiminoacetic acid, ethyl ester (20.1 g, 54.6 mmol) was dissolved in ethanol (200 mL) and treated with 2 equivalents of sodium hydroxide pellets (4.37 g, 110 mmol). Dissolution gradually occurred and the solution was stirred at room temperature for overnight. The ethanol was concentrated in vacuo and the viscous liquid was taken up in water and acidified (pH 3.0) with concentrated HCl. The product was extracted from the aqueous media with 2 portions of ethyl acetate, which were combined and washed with brine, dried (MgSO$_4$), and filtered. The filtrate was concentrated in vacuo to give 17.5 g (94%) of 2-(2-dodecyl -2H-tetrazol-5-yl)-2-methoxyimino-acetic acid as a viscous liquid;

$^1$H NMR (CDCl$_3$): δ 4.7 (t, 2H), 4.2 (s,3H), 2.0 (m, 2H), 1.4 (bs, 4H), 1.2 (s, 14H), 0.9 t, 3H) ppm.

(e) The acid (16.1 g, 47.4 mmol) from (d) was dissolved in dichloromethane (200 mL) and treated with 2,6-diisopropylaniline (8.4 g, 47.4 mmol) in a single portion. The solution was cooled to −10° C. followed by the addition of DCC (9.7 g, 47.4 mmol) with vigorous stirring. Precipitation occurred and the suspension gradually warmed to room temperature with stirring for overnight. Ethyl acetate (300 mL) was added, the suspension was filtered, and the filtrate was washed with aqueous NaOH (1 M), brine, dried (MgSO$_4$), and filtered. The filtrate was concentrated in vacuo leaving a mixture of the syn and anti-isomers. The mixture was separated using silica gel chromatography (elution with 20% ethyl acetate/80% hexane) to give 12.6 g (53%)of E-N-(2,6-diisopropylphenyl) -2-(2-dodecyl-2H-tetrazol-5-yl)-2-methoxyimino-acetamide (mp 75°–76° C.).

EXAMPLE 14

The appropriate fractions from the chromatography described in Example 13 were combined and the solvent was removed by evaporation under reduced pressure to provide 2.9 g (3.8%) of Z-N-(2,6-diisopropylphenyl) -2-(2-dodecyl-2H-tetrazol-5-yl)-2-methoxyiminoacetamide;

$^1$H NMR (CDCl$_3$): δ 7.4 (s, 1H), 7.3 (m, 1H), 7.2 (d, 2H), 5.7 (t, 2H), 4.2 (s, 3H), 3.4 (m, 2H), 2.0 (m, 2H), 1.4 (bs, 4H), 1.2 (m, 26H), 0.9 (t, 3H) ppm.

EXAMPLE 15

E-2-(2-Dodecyl-2H-tetrazol-5-yl)-2-methoxyimino -N-(2,4,6-trimethoxyphenyl)-acetamide When in the procedure of Example 13 (e) an appropriate amount of 2,4,6-trimethoxyaniline was substituted for 2,6-diisopropylaniline and the general procedure of Example 13 (e) was followed, E-2-(2-dodecyl -2H-tetrazol-5-yl)-2-methoxyimino-N-(2, 4, 6-trimethoxyphenyl)-acetamide was obtained, exclusively as the anti-isomer, mp 84°–85° C.

EXAMPLE 16

E-N-(2,6-Diisopropylphenyl)-2-(2-(1-methylundecyl) -2H-tetrazol-5-yl)-2-methoxyimino-acetamide When in the procedure of Example 13 (c) an appropriate amount of the mesylate of 2-dodecanol was substituted for 1-bromododecane and the general procedures for Example 13 (c), (d), and (e) were followed, E-N-(2,6-diisopropylphenyl)-2-(2-(1-methylundecyl) -2H-tetrazol-5-yl)-2-methoxyimino-acetamide was obtained;

$^1$H NMR (CDCl$_3$): δ 8.1 (bs, 1H), 7.3 (m, 1H), 7.2 (d, 2H), 5.0 (m, 1H), 4.2 (s, 3H), 3.2 (m, 2H), 2.1–1.9 (m, 2H), 1.7 (d, 3H), 1.3 (s, 16H), 1.2 (d, 12H), 0.9 (t, 3H) ppm.

EXAMPLE 17

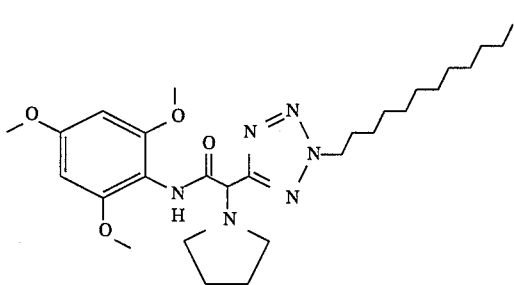

(±)-N-(2, 4, 6-trimethoxyphenyl)-2-(2-dodecyl -2H-tetrazol-5-yl)-2-pyrrolidia-1-yl-acetamide By following the general procedure of Example 1, α-bromo-2-dodecyltetrazol-5-yl-acetic acid was reacted with 2,4,6-trimethoxyaniline and DCC to provide (±)-N-2, 4,6-trimethoxyphenyl-2-(2-dodecyl-2H-tetrazol-5-yl) -2-bromo-acetamide. The bromo-acetamide (1.2 g, 2.21 mmol) was reacted with pyrrolidine (0.31 g, 4.43 mmol) in 15 mL of THF to provide, following purification by silica gel chromatography (eluting with ethyl acetate) 0.97 g (83%) of (±)-N-(2,4,6-trimethoxyphenyl) -2-(2-dodecyl- 2H- tetrazol-5-yl)-2-pyrrolidin -1-yl-acetamide, mp 66°–68° C.;

$^1$H NMR (CDCl$_3$): δ 8.4 (bs, 1H), 6.1 (s, 2H), 4.8 (bs, 1H), 4.6 (t, 2H), 3.8 (d, 9H), 2.8 (bs, 2H), 2.6 (bs, 2H), 2.0 (m, 2H), 1.8 (bs, 4H), 1.3 (bs, 4H), 1.2 (s, 4H), 0.9 (t, 3H) ppm;

Analysis calculated for C$_{28}$H$_{46}$N$_6$O$_4$: C, 63.37; H, 8.74; N, 15.84. Found: C, 63.30; H, 8.71; N, 15.87.

EXAMPLE 18

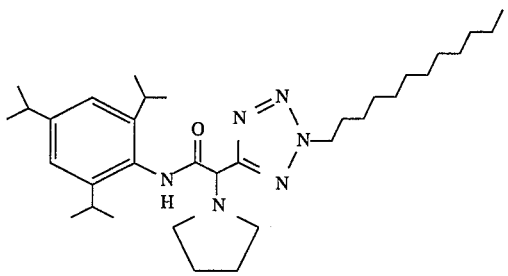

(±)-N-2,4,6-triisopropylphenyl-2-(2-dodeyl-2H-tetrazol -5-yl)-2-pyrrolidin-1-yl-acetamide By following the general procedure of Example 1, α-bromo-2-dodecyltetrazol-5-yl-acetic acid was reacted with 2,4,6-triisopropylaniline and DCC to provide (±)-N-2, 4,6-triisopropylphenyl-2-(2-dodecyl -2H-tetrazol-5-yl)-2-bromo-acetamide. The bromoacetamide (1.9 g, 3.31 mmol) was reacted with (0.47 g, 6.62 mmol) of pyrrolidine in 20 mL of THF to afford, following chromatography over silica gel, eluting with 5% ethyl acetate/75% hexane (V/V), 1.17 g (60%) of (±)-N-2,4, 6-triisopropylphenyl-2-(2-dodecyl -2H-tetrazol-5-yl)-2-pyrrolidin-1-yl-acetamide, mp 62°–64° C.;

$^1$H NMR (CDCl$_3$): δ 8.6 (bs, 1H), 7.0 (s, 2H), 4.7 (s, 1H), 4.6 (t, 2H), 3.1 (m, 2H), 2.9 (m, 1H), 1.8 (bs, 2H), 1.6 (bs, 2H), 2.0 (m, 2H), 1.8 (bs, 4H), 1.3 (bs, 4H), 1.2 (s, 14H), 1.2–1.1 (dd, 18H), 0.9 (t, 3H) ppm;

Analysis calculated for C$_{34}$H58N$_6$O: C, 72.04; H, 10.31; N, 14.83. Found: C, 72.25; H, 10.41; N, 15.04.

By following the general procedures of Example 1, the following compounds are prepared by reacting an α-bromotetrazole-acetic acid with an aryl amine and DCC to give an N-aryl-2-tetrazolyl-2-bromo-acetamide, which is then reacted with an amine.

EXAMPLE 19

(±)-N-(2,4,6-trimethylphenyl)-2-(2-ethyl-2H-tetrazol
-5-yl)-2-pyrrolidin-1-yl-acetamide

EXAMPLE 20

(±)-N-(2,4,6-trimethylphenyl)-2-(2-dodecyl-2H-tetrazol
-5-yl)-2-pyrrolidin-1-yl-acetamide

EXAMPLE 21

(±)-N-(4-isopropyl-6-chloro-8-methoxynaphth-2-yl)
-2(2-oct-3-enyl-2H-tetrazol-5-yl)-2-thiomorpholin-4-yl)-acetamide

EXAMPLE 22

(±)-N-(2,6-diisopropylphenyl)-2-(2-dodecyl-2H-tetrazol
-5-yl)-2-(homopiperidin-1-yl)-acetamide

EXAMPLE 23

By following the general procedure of Example 12, N-(2,6-diisopropylphenyl)-2-(2-dodecyl-2H-tetrazol -5-yl)-2-oxo-acetamide (1 g, 2.12 mmol) was dissolved in mL of ethanol. A mixture of 6 mL of pyridine containing ethoxyamine hydrochloride (1 g, 10.2 mmol) was added in one portion. The solution was heated at reflux for 1 hour, cooled to 24° C., and stirred for hours. The mixture was concentrated to dryness in vacuo, and the residue was dissolved in 50 mL of ethyl acetate and washed with 20 mL of 1N hydrochloric acid. The organic layer was washed with brine, dried (MgSO$_4$) filtered and the solvent was removed by evaporation to give an oil. The oil was purified by chromatography over silica gel (eluting with 85% hexane/ 15% ethyl acetate (V/V) to provide 0.19 g of a solid, identified as Z-N-(2,6-diisopropylphenyl) -2-(2-dodecyl-2H-tetrazol-5-yl)-2-ethoxyimino-acetamide;
$^1$H NMR (CDCl$_3$) (of the solid): δ 8.2 (s, 1H), 7.3 (m, 1H), 7.2 (d, 2H), 4.7 (t, 2H), 4.4 (q, 2H), 3.2 (m, 2H), 2.0 (m, 2H), 1.4 (t, 3H), 1.3 (bs, 4H), 1.2 (m, 26H), 0.9 (t, 3H) ppm;

EXAMPLE 24

By following the general procedure of Example 23, the following compounds are prepared. The appropriate fractions from the chromatography described in Example 23 were combined and concentrated to dryness to give 0.37 g of an oil identified as the E-isomer of N-(2,6-diisopropylphenyl)-2-(2-dodecyl-2H-tetrazol -5-yl)-2-ethoxyimino-acetamide;
$^1$H NMR (CDCl$_3$): δ 7.4 (m, 2H), 7.2 (d, 2H), 4.7 (t, 2H), 4.5 (q, 2H), 3.4 (m, 2H), 2.0 (m, 2H), 1.4 (t, 3H), 1.4 (s, 4H), 1.3 (m, 26H), 0.9 (t, 3H) ppm.

EXAMPLE 25

N-(2-methoxy-4-bromo-6-methylthiophenyl)-2-(2-ocyl
-2H-tetrazol-5-yl)-2-isobutoxyimino-acetamide

EXAMPLE 26

N-(1-naphthyl)-2-(2-isoheptyl-2H-tetrazol-5-yl)
-2-isopropoxyimino-acetamide

EXAMPLE 27

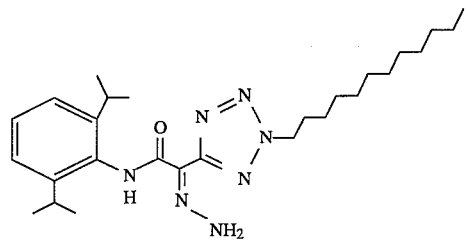

N-(2,6-diisopropylphenyl)-2-(2 dodecyl-2H-tetrazol
-5-yl)-2-hydrazono-acetamide

To a solution of N-(2,6-diisopropylphenyl)-2 -(2-dodecyl-2H-tetrazol-5-yl)-2-oxo-acetamide (0.85 g, 1.8 mmol) in 30 mL of ethanol were added 0.113 mL of hydrazine (3.6 mmol). The solution was heated at reflux for 4 hours, cooled to 24° C., and concentrated to dryness by removal of solvents under reduced pressure to give an oil. The oil was dissolved in 50 mL of ethyl acetate, washed with water and brine, dried (MgSO$_4$), and concentrated to dryness to afford 1.3 g of an oil. The oil was further purified by chromatography over silica gel, eluting with 25% ethyl acetate/ 75% hexane (V/V) to provide 0.52 g of (±)-N-(2,6-diisopropylphenyl)-2-(2-dodecyl-2H-tetrazol -5-yl)-2-hydrazono-acetamide;

$^1$H NMR (CDCl$_3$): δ 7.2–7.4 (m, 3H), 4.7 (t, 2H), 3.1 (m, 2H), 2.1 (t, 2H), 1.1–1.4 (m, 30H), 0.9 (m, 3H), ppm.

The following imines are prepared by the general procedure of Example 27.

EXAMPLE 28

N-(2,6-diisopropylphenyl)-2-(2-dodecyl-2H-tetrazol-5-yl)-2-phenylhydrazono-acetamide $^1$H NMR (CDCl$_3$): δ 7.05–7.4 (m, 9H), 4.7 (m, 2H), 3.1 (m, 2H), 2.1 (m, 2H), 1.1–1.4 (m, 18H), 0.9 (t, 3H).

EXAMPLE 29

N-(2,6-diisopropylphenyl)-2-(2-dodecyl-2H-tetrazol-5-yl)-2-dimethylhydrazono-acetamide $^1$H NMR (CDCl$_3$): δ 7.05–7.4 (m, 9H), 4.7 (m, 2H), 3.1 (m, 2H), 2.1 (m, 2H), 1.1–1.4 (m, 18H), 0.9 (t, 3H).

EXAMPLE 30

N-(2,6-diisopropylphenyl)-2-(2-dodecyl-2H-tetrazol-5-yl)-2-aminocarbonylhydrazono-acetamide

EXAMPLE 31

N-(6-ethylthionaphth-1-yl)-2-(2-octyl-2H-tetrazol-5-yl)-2-ethylhydrazono-acetamide

EXAMPLE 32

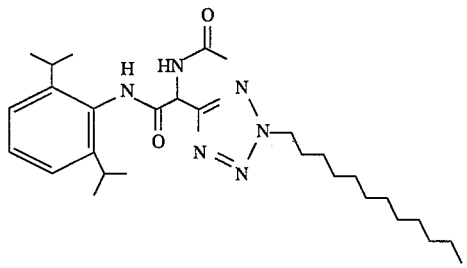

(±)-N-(2,6-diisopropylphenyl)-2-(2-dodecyl-2H-tetrazol-5-yl)-2-acetylamino-acetamide Triethylamine (0.27 g, 2.75 mmol) was added in one portion to a stirred solution of 1.3 g (2.75 mmol) of (±)-N-(2,6-diisopropylphenyl)-2-(2-dodecyl-2H-tetrazol-5-yl)-2-amino-acetamide (prepared as in Example 10) in 50 mL of THF. To the solution was added in one portion 0.23 g (3.0 mmol) of acetyl chloride. The mixture was stirred at 24° C. for 15 minutes, diluted with 50 mL of ethyl acetate, washed with 50 mL of 1N hydrochloric acid, then with 50 mL of 1N sodium hydroxide, brine, and finally dried over MgSO$_4$. The solution was filtered and concentrated by removing the solvents in vacuo to afford an oil. The oil was further purified by chromatography over silica gel (eluting with 1:1 ethyl acetate/hexane) to provide 0.65 g of (±)-N-(2,6-diisopropylphenyl)-2-(2-dodecyl-2H-tetrazol-5-yl)-2-acetylamino-acetamide;

$^1$H NMR (CDCl$_3$): δ 7.8 (s, 1H), 7.3 (t, 1H), 7.2 (d, 2H), 7.1 (d, 1H), 6.2 (d, 1H), 4.6 (t, 2H), 2.8 (bs, 2H), 2.2 (s, 3H), 2.0 (m, 2H), 1.4 (s, 4H), 1.3 (s, 4H), 1.1 (s, 12H), 0.9 (t, 3H) ppm;

Analysis calculated for C$_{29}$H$_{48}$N$_6$O$_2$: C, 67.93; H, 9.44; N, 16.39. Found: C, 67.72; H, 9.20; N, 16.48.

By following the general procedures of Example 32, the following acylated 2-aminoamides are prepared.

EXAMPLE 33

(±)-N-(2-α-butylthionaphth-1-yl-2-(3-isoheptyl-3H-tetrazol-5-yl)-2-formamido-acetamide

EXAMPLE 34

(±)-N-(4-(2-chlorophenyl)-5,7-dimethylquinolin-3-yl)-2-[3-(5-heptadecen-1-yl)-3H-tetrazol-5-yl]-2-propanamido-acetamide

EXAMPLE 35

(±)-N-(2,4-dimethylthio-6-methylpyrimidin-3-yl)-2-(2-(2,2-dimethyldodecyl)-2H-tetrazol-5-yl)-2-acetylamino-acetamide

EXAMPLE 36

(±)-N-(2,6-diisopropylphenyl)-2-(2-dodecyl-2H-tetrazol-5-yl)-2-cyclohexylamino-acetamide Cyclohexylamine (0.36 g, 3.67 mmol) was added in one portion to a stirred solution of 1 g (1.84 mmol) of (±)-N-(2,6-diisopropylphenyl)-2-(2-dodecyl-2H-tetrazol-5-yl)-2-bromo-acetamide (prepared as in Example 1 (e)) in 10 mL of THF. The solution was heated at reflux for 6 hours, cooled to 24° C., and stirred for 48 hours. The solvent was removed by evaporation under reduced pressure to give an oil. The oil was purified by chromatography over silica gel (eluting with ethyl acetate/hexane 1:3 V/V) to provide 0.54 g of a white solid identified as (±)-N-(2,6-diisopropylphenyl) -2-(2-dodecyl-2H-tetrazol-5-yl)-2-cyclohexylaminoacetamide;

$^1$H NMR (CDCl$_3$): δ 9.1 (s, 1H), 7.3 (t, 1H), 7.2 (d, 2H), 4.9 (bs, 1H), 4.6 (t, 2H), 3.0 (m, 2H), 2.6 (bs, 1H), 2.3 (bs, 1H), 2.0 (m, 4H), 1.8 (m, 2H), 1.6 (m, 2H), 1.4 (s, 4H), 1.3 (s, 18H), 0.9 (t, 3H) ppm;

Analysis calculated for C$_{33}$H$_{56}$N$_6$O: C, 71.69; H, 10.21; N, 15.20. Found: C, 71.88; H, 9.95; N, 15.29.

The following compounds are prepared by reacting an amine with a 2-bromo-acetamide pursuant to the general procedure of Example 36.

EXAMPLE 37

(±)-N-(2,4,6-trichlorophenyl)-2-[2-(5-octen-1-yl) -2H-tetrazol-5-yl]-2-isopropylamino-acetamide

EXAMPLE 38

(±)-N-(4-nitrophenyl)-2-(2-heptyl-2H-tetrazol-5-yl) -2-(N-methylcyclopentylamino)-acetamide

EXAMPLE 39

(±)-N-(7-hydroxynaphth-2-yl)-2-[2-(5-isobutyloctyl) -2H-tetrazol-5-yl]-2-(N-ethylcyclopropylamino)- acetamide

EXAMPLE 40

(±)-N-phenyl-2-(2-methyl-2H-tetrazol-5-yl)-2- phenylamino-acetamide

EXAMPLE 41

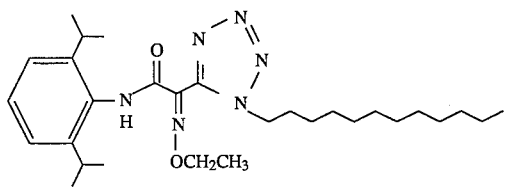

E-N-(2,6-Diisopropylphenyl)-2-(1-dodecyl-1H-tetrazol -5-yl)-2-ethoxyimino-acetamide To a stirred solution of 9.42 g (26.6 mmol) of 2-(1- dodecyl-1H-tetrazol-5-yl)-2-ethoxyimino-acetic acid in 125 mL of dichloromethane were added in one portion 4.96 g (27.9 mmol) of 2,6-diisopropylaniline. The solution was cooled to −10° C., and 5.75 g (27.9 mmol) of dicyclohexy- lcarbodiimide were added in one portion. The mixture was stirred under nitrogen at −10° C. for 3 hours, and then allowed to warm to 25° C. over 10 hours. The reaction mixture was diluted with 56 mL of ethyl acetate, filtered to remove the solid precipitate, and the filtrate was washed with 50 mL of 1M aqueous sodium hydroxide, 50 mL of brine, dried over $MgSO_4$, filtered, and the solvent was removed from the filtrate by evaporation under reduced pressure to give a viscous oil. The oil was purified by chromatography over silica gel, eluting with ethyl acetate: hexane (1:4 v/v). Fractions shown to contain one compo- nent were combined and concentrated to dryness to give 10.5 g (77% yield) of product identified as (E)-N-(2,6- diisopropylphenyl)-2-(1-dodecyl-1H-tetrazol -5-yl)-2- ethoxyimino-acetamide;

$^1$H NMR (CDCl$_3$): δ 8.1 (s, 1H), 7.3 (m, 1H), 7.2 (d, 2H), 4.4 (q, 2H), 4.3 (t, 2H), 3.1 (m, 2H), 1.9 (m, 2H), 1.4 (t, 3H), 1.2 (m, 30H), 0.9 (t, 3H)ppm.

Remaining fractions contained the Z-isomer which was not isolated.

EXAMPLE 42

(E)-N-(2,6-Diisopropylphenyl)-2-(2-dodecyl-2H-tetrazol -5-yl)-2-phenylmethoxyimino-acetamide To a stirred solution of 2 g (4.25 mmol) of N-(2,6- diisopropylphenyl)-2-(2-dodecyl-2H-tetrazol -5-yl)-2-oxo- acetamide (prepared as described in Example 11) in 12 mL of ethanol were added in one portion 2 g (12.5 mmol) of O-benzylhydroxylamine. The mixture was diluted with 12 mL of pyridine and heated at reflux for 1 hour. The mixture was cooled to 25° C., diluted with 250 mL of ethyl acetate, and washed with 50 mL of 1M aqueous hydrochloric acid, 50 mL of brine, dried over $MgSO_4$, and filtered. The filtrate was concentrated to dryness to give a viscous oil. The oil was purified by chromatography over silica gel, eluting with ethyl acetate:hexane (1:4 v/v). Fractions containing one component were combined and the solvent was removed to afford 0.45 g of a white solid identified as (E)-N-(2,6- diisopropylphenyl)-2 -(2-dodecyl-2H-tetrazol-5-yl)-2-phe- nylmethoxyiminoacetamide, mp 73°–74° C.

EXAMPLE 43

The remaining fractions from Example 42 were combined and the solvent was removed by evaporation under reduced pressure to give 1.03 g of (Z)-N-(2,6-diisopropylphenyl)-2- (2-dodecyl-2H-tetrazol-5-yl) -2-phenylmethoxyimino-ac- etamide, MS m/e 576.

Analysis calculated from $C_{34}H_{50}N_6O_2$: C, 71.05; H, 8.77; N, 14.62. Found: C, 71.02; H, 8.61; N, 14.59.

EXAMPLE 44

A pharmaceutical formulation in the form of hard gelatin capsules for oral administration are prepared using the following ingredients:

|  | Quantity (mg/capsule) |
| --- | --- |
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is (±)-N-(2,6-diethylphenyl)-2-(2-heptyl-2H-tetrazol-5-yl)-2- ethoxyimino-acetamide.

EXAMPLE 45

Formulation for Oral Suspension

| Ingredient | Amount |
| --- | --- |
| (±)-N-(6-chloronaphth-1-yl)-2- (2-isoheptyl-2H-tetrazol-5-yl)-2- (N,N-diethylamino)-acetamide | 500 mg |
| Sorbitol solution (70% N.F.) | 40 mL |
| Sodium benzoate | 150 mg |
| Saccharin | 10 mg |
| Cherry flavor | 50 mg |
| Distilled water q.s. ad | 100 ML |

The sorbitol solution is added to 40 mL of distilled water and the tetrazole acetamide is suspended therein. The saccharin, sodium benzoate, and flavoring are added and dissolved. The volume is adjusted to 100 mL with distilled water. Each milliliter of syrup contains 5 mg of active ingredient.

EXAMPLE 46

Tablets each containing 60 mg of active ingredient.

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1.0 mg |
| Total | 150 mg |

The active ingredients, starch and cellulose, are passed through a No. 45 mesh U.S. sieve and mixed thoroughly. The solution of polyvinylpyrrolidone is mixed with the resultant powders and then passed through a No. 14 mesh U.S. sieve. The granules are dried at 50°–60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 13.

We claim:

1. A compound having the Formula I

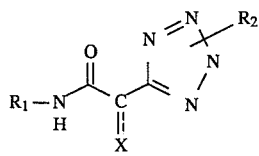

wherein $R_1$ is selected from
(a) phenyl which is unsubstituted or is substituted with from 1 to 3 substituents selected from
$C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$, wherein m is 0 or 1, and each of $R_x$ and $R_y$ is independently hydrogen or $C_1$–$C_4$ alkyl;

X is unsaturated (=X) and is selected from:
(a) =O
(b) =$NR_5$ where $R_5$ is selected from
(i) the group $R_4$, wherein $R_4$ is hydrogen, $C_1$–$C_4$ alkyl, hydroxy $C_1$–$C_4$ alkyl, $C_1$–$C_4$ alkanoyl, $C_3$–$C_{10}$ cycloalkyl, $C_2$–$C_6$ alkenyl, or $(CH_2)_m$-phenyl or

wherein m is 0 or 1 and the phenyl is unsubstituted or is substituted with from 1 to 3 substituents selected from
$C_1$–$C_4$ alkyl,
$C_1$–$C_4$ alkoxy,
$C_1$–$C_4$ alkylthio,
phenyl,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$, wherein m is 0 or 1, and each of $R_x$ and $R_y$ is hydrogen or a straight chain alkyl group having 1 to 4 carbon atoms;

$R_4$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with an alkyl group having from 1 to 4 carbon atoms and the N-oxides thereof;

or 1- or 2-naphthyl which is unsubstituted or substituted with 1 to 3 substituents selected from
alkyl having from 1 to 4 carbon atoms and which is straight or branched, and
alkoxy having from 1 to 4 carbon atoms and which is straight or branched;

(ii) the group —$OR_x$, wherein $R_x$ is hydrogen, $R_4$, $C_1$–$C_4$ alkyl, $C_2$–$C_{18}$ alkenyl, $C_2$–$C_{18}$ alkynyl, or such alkyl, alkenyl, and alkynyl groups substituted with $R_4$;

(iii) the group —$NR_6 R_7$, wherein $R_6$ is hydrogen, $C_1$–$C_4$ alkyl, or phenyl which is unsubstituted or substituted with 1 to 3 substituents selected from straight or branched alkyl having 1 to 4 carbon atoms, straight or branched alkoxy having 1 to 4 carbon atoms, halo, trifluoromethyl, cyano, and nitro; $R_7$ is hydrogen, $C_1$–$C_4$ alkyl, or heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with an alkyl group having from 1 to 4 carbon atoms and the N-oxides thereof; or $R_6$ and $R_7$ together with the nitrogen to which they are attached from a 4- to 7-membered ring;

(iv) or $NHCONH_2$;

wherein X is saturated (—X), it is selected from the group $NR_3 R_4$, wherein $R_4$ is as defined above, or $R_3$ and $R_4$ are the same or different and are selected from
(a) hydrogen;
(b) $C_1$–$C_4$ alkyl or a cycloalkyl group having from 3 to 10 carbon atoms;
(c) when $R_3$=H, $R_4$ is $C_1$–$C_4$ alkanoyl, benzoyl, substituted benzoyl, $C_2$–$C_6$ alkenyl, or $R_5$ (i) group as defined above;

(d) $R_3$ and $R_4$ taken together with the nitrogen atom to which they are attached to form 5- to 7-membered monocyclic heterocycles containing 1 to 4 heteroatoms, said heteroatoms being nitrogen, oxygen, or sulfur and combinations thereof, said heterocyclic group being unsubstituted or substituted with phenyl or an alkyl group having 1 to 4 carbon atoms; wherein $R_2$ is a straight or branched hydrocarbon chain having from 1 to 20 carbon atoms and is saturated or is unsaturated and has one double bond or has two nonadjacent double bonds; and wherein $R_2$ can be bonded directly to the tetrazole ring or connected through an oxygen or sulfur atom; pharmaceutically acceptable salts and individual enantiomeric isomers and regioisomers of the compounds.

2. A compound of claim 1 wherein $R_1$ is phenyl or substituted phenyl.

3. A compound of claim 2 wherein $R_2$ is $C_1$–$C_{20}$ alkyl.

4. A compound of claim 3 wherein $R_2$ is $C_6$–$C_{12}$ alkyl.

5. A compound of claim 4 wherein X is —$NR_3R_4$.

6. A compound of claim 5 which is:

(±)-N-(2,6-diisopropylphenyl)-2-(2-dodecyl -2H-tetrazol-5-yl)-2-thiomorpholin-4-yl-acetamide;

(±)-N-(2,6-diisopropylphenyl)-2-(2-dodecyl -2H-tetrazol-5-yl)-2-morpholino-4-yl-acetamide;

(±)-N-(2,6-diisopropylphenyl)-2-(2-dodecyl -2H-tetrazol-5-yl)-2-piperidin-1-yl-acetamide;

(±)-N-(2,6-diisopropylphenyl)-2-(2-dodecyl -2H-tetrazol-5-yl)-2-pyrrolidinyl-1-yl-acetamide;

(±)-N-(2,6-diisopropylphenyl)-2-(2-dodecyl -2H-tetrazol-5-yl)-2-imidazol-1-yl-acetamide;

(±)-N-(2,6-diisopropylphenyl)-2-(2-dodecyl -2-tetrazol-5-yl)-2-(4-methyl-piperazin-1-yl)-acetamide;

(±)-2-diethylamino-N-(2,6-diisopropylphenyl) -2-(2-dodecyl-2H-tetrazol-5-yl)-acetamide;

(±)-2-[bis-(2-hydroxyethyl)-amino] -N-(2,6-diisopropylphenyl)-2-(2-dodecyl-2H-tetrazol-5-yl)-acetamide;

(±)-N-(2,6-diisopropylphenyl)-2 -dimethylamino-(2-dodecyl-2H-tetrazol-5-yl)-acetamide;

(±)-2-amino-N-(2,6-diisopropylphenyl)-2-(2 -dodecyl-2H-tetrazol-5-yl)-acetamide;

(±)-N-(2,4,6-trimethoxyphenyl)-2-(2-dodecyl -2H-tetrazol-5-yl)-2-pyrrolidin-1-yl-acetamide;

(±)-N-2,4,6-triisopropylphenyl-2-(2-dodecyl -2H-tetrazol-5-yl)-2-pyrrolidin-1-yl-acetamide;

(±)-N-(2,4,6-trimethylphenyl)-2-(2-dodecyl -2H-tetrazol-5-yl)-2-pyrrolidin-1-yl-acetamide;

(±)-N-(2,6-diisopropylphenyl)-2-(2-dodecyl -2H-tetrazol-5-yl)-2-(homopiperidin-1-yl) acetamide;

(±)-N-(2,6-diisopropylphenyl)-2-(2-dodecyl -2H-tetrazol-5-yl)-2-cyclohexylamino-acetamide;

(±)-N-(2,4,6-trichlorophenyl)-2-[2-(5-octen -1-yl)-2H-tetrazol-5-yl]-2-isopropylaminoacetamide; or (±)-N-(4-nitrophenyl)-2-(2-heptyl -2H-tetrazol-5-yl)-2-(N-methylcyclopentylamino)-acetamide.

7. A compound of claim 4 wherein X is =N—$R_5$.

8. A compound of claim 7 which is

N-(2,6-diisopropylphenyl)-2-(2-dodecyl-2H -tetrazol-5-yl)-2-hydroxyimino-acetamide;

E-N-(2,6-diisopropylphenyl)-2-(2-dodecyl-2H -tetrazol-5-yl)-2-methoxyimino-acetamide;

Z-N-(2,6-diisopropylphenyl)-2-(2-dodecyl-2H -tetrazol-5-yl)-2-methoxyimino-acetamide;

E-2-(2-dodecyl-2H-tetrazol-5-yl)-2 -methoxyimino-N-(2,4,6-trimethoxyphenyl)-acetamide;

E-N-(2,6-diisopropylphenyl)-2-(2-(1-methylundecyl) -2H-tetrazol-5-yl)-2-methoxyiminoacetamide;

Z-N-( 2,6-diisopropylphenyl)-2-(2-dodecyl -2H-tetrazol-5-yl)-2-ethoxyimino-acetamide;

E-N-( 2,6-diisopropylphenyl)-2-(2-dodecyl -2H-tetrazol-5-yl)-2-ethoxyimino-acetamide;

E-N-( 2,6-diisopropylphenyl)-2-(1-dodecyl -1H-tetrazol-5-yl)-2-ethoxyimino-acetamide;

N-(2,4,6-triisopropylphenyl-2-(2-dodecyl -2H-tetrazol-5-yl)-2-methoxyimino-acetamide;

N-(2-methoxy-4-bromo-6-methylthiophenyl) -2-(2-ocyl-2H-tetrazol-5-yl)-2-isobutoxyimino-acetamide;

N-(2,6-diisopropylphenyl)-2-(2 dodecyl -2H-tetrazol-5-yl)-2-hydrazono-acetamide;

N-( 2,6-diisopropylphenyl)-2-(2-dodecyl -2H-tetrazol-5-yl)-2-phenylhydrazono-acetamide;

N-( 2,6-diisopropylphenyl)-2-(2-dodecyl -2H-tetrazol-5-yl)-2-dimethylhydrazono-acetamide;

Z-N-(2,6-diisopropylphenyl)-2-(2-dodecyl -tetrazol-5-yl)-2-(phenylmethoxyimino)-acetamide;

E-N-(2,6-diisopropylphenyl)-2-(2-dodecyl-2H -tetrazol-5-yl)-2-(phenylmethoxyimino)-acetamide; or N-(2,6-diisopropylphenyl)-2-(2-dodecyl -2H-tetrazol-5-yl)-2-aminocarbonylhydrazono-acetamide.

9. A compound of claim 1 wherein X is —$NR_3R_4$ wherein $R_3$ and $R_4$ independently are hydrogen, $C_1$–$C_4$ alkyl, $C_3$–$C_6$ cycloalkyl, hydroxy $C_1$–$C_4$ alkyl, or $R_3$ and $R_4$ taken together with the nitrogen form pyrrolidinyl, morpholinyl, piperidinyl, thiomorpholinyl, 4-alkylpiperazinyl, or imidazolyl.

10. A compound of claim 1 wherein X is —$NR_3R_4$ in which $R_3$ is hydrogen and $R_4$ is $C_1$–$C_4$ alkyl or $C_1$–$C_4$ alkanoyl.

11. A compound of claim 1 wherein X is =N—$R_5$.

12. A compound of claim 11 wherein $R_5$ is hydroxy or $C_1$–$C_4$ alkoxy.

13. A compound of claim 4 wherein $R_1$ is 2,6-diisopropylphenyl and $R_2$ is dodecyl.

14. A compound of claim 2 wherein $R_1$ is phenyl substituted with one, two, or three $C_1$–$C_4$ alkyl groups.

15. A pharmaceutical formulation for treating hypercholesterolemia or atherosclerosis comprising an ACAT-inhibiting effective amount of a compound of claim 1 together with a pharmaceutically acceptable carrier.

16. A formulation of claim 15 wherein $R_1$ is phenyl or substituted phenyl and $R_2$ is $C_6$–$C_{12}$ alkyl.

17. A formulation of claim 16 wherein $R_1$ is 2,6-diisopropylphenyl.

18. A formulation of claim 17 wherein $R_2$ is dodecyl.

19. A method of treating hypercholesterolemia or atherosclerosis comprising administering to a mammal in need of such treatment an ACAT-inhibiting amount of a compound of claim 1.

20. A method of claim 19 employing a compound wherein $R_1$ is phenyl or substituted phenyl and $R_2$ is $C_6$–$C_{12}$ alkyl.

21. A method of claim 20 employing a compound wherein $R_1$ is 2,6-diisopropylphenyl and $R_2$ is dodecyl.

22. A compound having the Formula I

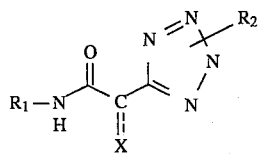

wherein $R_1$ is selected from
(a) phenyl which is unsubstituted or is substituted with from 1 to 3 substituents selected from
$C_1-C_4$ alkyl,
$C_1-C_4$ alkoxy,
$C_1-C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$, wherein m is 0 or 1, and each of $R_x$ and $R_y$ is independently hydrogen or $C_1-C_4$ alkyl;
X=O; and
$R_2$ is a straight or branched hydrocarbon chain having from 1 to 20 carbon atoms and is saturated or is unsaturated and has one double bond or has two nonadjacent double bonds; and wherein $R_2$ can be bonded directly to the tetrazole ring or connected through an oxygen or sulfur atom; pharmaceutically acceptable salts and individual enantiomeric isomers and regioisomers of the compounds.

23. The compound N-(2,6-diisopropylphenyl)-2-(2-dodecyl-2H-tetrazol -5-yl)-2-oxo-acetamide.

\* \* \* \* \*

UNITED STATES PATENT AND TRADEMARK OFFICE
CERTIFICATE OF CORRECTION

PATENT NO. : 5,461,049
DATED : October 24, 1995
INVENTOR(S) : O'Brien, et. al.

It is certified that error appears in the above-indentified patent and that said Letters Patent is hereby corrected as shown below:

Column 32, line 37 at the end of the line, "$C_1$-$C_4$" should read "$C_1$-$C_{18}$".

Column 32, line 66, "group " should read "groups".

Signed and Sealed this

Seventh Day of May, 1996

Attest:

BRUCE LEHMAN

Attesting Officer

Commissioner of Patents and Trademarks